United States Patent [19]
Hara

[11] Patent Number: 5,035,888
[45] Date of Patent: Jul. 30, 1991

[54] THERAPEUTICALLY USEFUL MINERAL COMPOSITION

[76] Inventor: Tadataka Hara, 4-31-15 Hamadayama, Suginami-ku, Tokyo 168, Japan

[21] Appl. No.: 433,385

[22] Filed: Nov. 6, 1989

Related U.S. Application Data

[63] Continuation of Ser. No. 270,421, Nov. 9, 1988, abandoned, which is a continuation of Ser. No. 183,280, Apr. 11, 1988, abandoned, which is a continuation of Ser. No. 83,000, Aug. 5, 1987, abandoned, which is a continuation of Ser. No. 914,560, Oct. 2, 1986, abandoned, which is a continuation of Ser. No. 745,928, Jun. 20, 1985, abandoned, which is a continuation of Ser. No. 679,601, Dec. 7, 1984, abandoned.

[51] Int. Cl.$^5$ .................. A61K 35/78; A61K 33/00
[52] U.S. Cl. .................. 424/195.1; 424/600; 424/601; 424/630; 424/639; 424/641; 424/648; 424/650; 424/715; 424/722; 424/724
[58] Field of Search .................. 424/195.1, 722, 715, 424/724, 650, 601, 630, 639, 641, 648

[56] References Cited

PUBLICATIONS

Puritan's Pride, p. 25, 1980.
Chem. Abst. 66:39075r, 1967.
Ch Abstract No. 149326z, vol. 79, 1973.

Primary Examiner—John W. Rollins

[57] ABSTRACT

The mineral composition is useful for treatment of blood acidosis, peritoneal ascites and anemia. It is a combination of particulate wood ash and calcium carbonate.

10 Claims, No Drawings

THERAPEUTICALLY USEFUL MINERAL COMPOSITION

This application is a continuation of application Ser. No. 270,421, filed Nov. 9, 1988 now abandoned and a continuation of Ser. No. 256,118, filed Oct. 7, 1988 now abandoned, which is a continuation of application Ser. No. 183,280, filed Apr. 11, 1988 now abandoned, which is a continuation of application Ser. No. 083,000, filed Aug. 5, 1987, now abandoned, which is a continuation of application Ser. No. 914,560, filed Oct. 2, 1986, now abandoned, which is a continuation of application Ser. No. 745,928 filed Jun. 20, 1985, now abandoned, which is a continuation of application Ser. No. 679,601, filed Dec. 7, 1984, now abandoned.

BACKGROUND OF THE INVENTION

The invention is related to a pharmaceutical mineral composition which is useful for therapeutic treatment of electrolyte imbalance of biological fluids. More specifically, the composition is a mixture of wood ash particles containing mineral compounds in combination with calcium carbonate.

Mammals, in particular humans, have body compositions which are of approximately fifty to seventy weight percent aqueous media. The aqueous fluids are distributed intra and extracellularly and enable liquid transfer of nutrients, enzymes, hormones, waste products and the like. The extracellular fluids include blood, lymph fluid, gastric juice, urine, bile, perspiration, etc. which all contain inorganic electrolyte salts. Intracellular fluids also contain electrolyte salts but the kinds and proportions differ from those of the extracellular fluids owing to the semipermeability of tissue membranes and cellular function.

The inorganic ions present in such electrolyte fluids play an integral part in the proper function of physiological processes. For example, sodium and potassium are necessary for nerve and cellular function. Iron and manganese are necessary for oxidative metabolism and calcium is utilized in bone. In general, inorganic ions usually are present in most physiological processes.

An imbalance of the distribution or proportions of physiological electrolyte ions present in a biological organism will produce pathological manifestations and malconditions therein. Nervous disorders, anemia, kidney disfunction, intestinal malabsorption, heart disease, muscle wasting, osteoporosis, cirrhosis, liver megoblasteomia and other organic diseases can develop if this occurs.

Metabolic acidosis or acidification of the blood can also occur as a result of electrolyte imbalance such as increased acid content or decreased alkali content in the electrolyte fluid or as a result of electrolyte impaired renal function. Acidosis, may have its origin in such diseases as diabetic ketoacidosis, alcoholic ketoacidosis or diarrhea, all of which in part are related to electrolyte imbalance. Acidosis, in turn, is manifested symptomatically as nausea, diarrhea, abdominal ascites, cerebral vasoconstriction, headache and gastrointestinal distress.

Electrolyte imbalance can moreover produce extracellular volume retention and antidiuretic effects. This, in turn, is manifested as tissue swelling and ascites, accumulation of fluid within the peritoneal cavity. A side effect of diseases such as neoplastic disease, peritoneal inflammatory disease, portal hypertension, hepatic congestion and hypoalbuminemia also is electrolyte imbalance and ascites. These symptoms present severe distress to a patient over and above the sickness caused by the underlying disease.

It is believed, therefore, that restoration of proper extracellular electrolyte balance will alleviate substantially the foregoing symptomatic malconditions associated with many diseases, namely anemia, acidosis and ascites. Accordingly, it is an object of the invention to discover a mineral composition which will provide a selection of the ions necessary to restore extracellular electrolyte balance. It is a further object to discover a mineral composition which has a proportional distribution of ions that will enable beneficial absorption by the gut. Yet another object is discovery of a single source for a composition having the full range of mineral ions necessary as human electrolyte salts.

SUMMARY OF THE INVENTION

These and other objects are achieved by the invention which is directed to an essential mineral composition. This pharmaceutical composition of essential minerals comprises wood ash particles of about 100 to 200 mesh in combination with calcium carbonate in a ratio of about 8:1 to about 9:1 respectively. When the composition is dissolved or dispersed in water, it will provide an aqueous medium having a pH of from about 9 to 11. The minerals present in the wood ash particles include inorganic compounds of calcium, magnesium, manganese, iron, potassium, sodium, silicon, copper, zinc, cobalt, titanium and chromium. The compounds may be present as oxides, halides or the oxidized forms of phosphorus and sulfur. In a preferred composition, these minerals are present as oxides and would include phosphorus and sulfur oxides.

The invention is further directed to methods for treatment of anemia and acidosis of the blood and for treatment of ascites. These methods are practical by administering by an oral route an effective amount pharmaceutical composition of the invention in the form of a pill, tablet, elixer, slurry or dispersion, which will promote therapeutic treatment.

DETAILED DESCRIPTION OF THE INVENTION

The mineral composition of the invention is a unitary source for a substantial number of the essential inorganic ions necessary in the human diet. The minerals are delivered in a manner which enables facile absorption by the gut. Moreover, it is believed that their distribution and proportions in the composition provide extra benefits in that these relationships influence absorption and utilization of the minerals.

The mineral composition is a physical mixture of particulate wood ash and particulate calcium carbonate. The wood ash delivers the minerals and these constituents have been found to occur naturally in the distribution and proportions which benefit absorption and utilization. The particulate size of the ash is from about 100 to 200 mesh but this is not essential to the nature of the composition. The ratio of ash to calcium carbonate is from about 8:1 to 9:1. The calcium carbonate serves to buffer partially the basicity of the ash and lowers the pH of the composition in water to about 9 to 11.

The minerals contributed by the wood ash may include the following inorganic oxides: calcium, magnesium, manganese, aluminum, iron, potassium, sodium, silicon, phosphorus, copper, zinc, cobalt, titanium, chromium and sulfur. In addition, halides such as chloride, bromide and iodide may be present. The composition may also contain trace amounts of cadmium and lead, however, these are usually not present. A typical composition may contain some or all of these minerals. The weight percentages of minerals in a typical composition will range as follows: calcium (oxide) about 25-35% from the ash and about 20-30% from the calcium carbonate, magnesium oxide about 7-8%, manganese oxide about 0.5 to 2%, ferric oxide about 0.5-5%, potassium oxide about 8-12%, sodium oxide about 1-3%, silicon dioxide about 0.5-1.5%, phosphorus oxide about 2-5%, copper oxide about 0.01-0.03%, zinc oxide about 0.03-0.06%, cobalt oxide about 0.0005-0.002%, titanium oxide about 0.2-0.4%, chromium oxide about 0.005-0.02%, sulfite about 2-5% and halide about 0.02-0.04%.

The wood ash is produced in an especial manner which facilitates the activity of the invention. To this end, whole deciduous, hardwood trees including the bark, leaves, wood pulp and roots are ground in a solid pulping apparatus such as a hammer mill, grist mill or the like. This finely ground woody material is then air dried by directing a stream of warm dry air through the material, by tumble drying under forced air conditions, by passively drying in, for example, shallow pans, or by drying in a similar manner. Following this, the dried material is combusted without an additional source of fuel and under conditions which supply a controlled quantity of oxygen or air but maintain the combustion of the burning material at a temperature less than 800° C. Typically, this is accomplished in a retort vessel with an oxygen or air supply and for which the temperature can be controlled by external cooling. Another method utilizes control of the temperature of the combusting air or oxygen so that after ignition of the dried material, its temperature is controlled within the allowed limits. A further method is open air slow combustion on a surface which can be cooled and will allow temperature control of the combustion.

The ash prepared in this manner is gathered and ground to a fine powder. The powder is sized through a screening device in order to separate that portion having a mesh of from about 100 to 200 U.S. standard sieve series.

The sized ash powder and powdered particulate calcium carbonate in the appropriate weight ratio are mixed by agitation, tumbling, ball milling or other means to produce the composition ready for processing into dosage form. Alternatively, the ash and carbonate may be mixed directly after ash production and the mixture ground and sized to the appropriate mesh.

The composition may be formulated into appropriate administrative forms such as pills, tablets, capsules, troches and the like. Incorporated into the formulation may also be additional binders, excipients, extenders, diluents, dispersing agents and absorption agents. Such materials are known in the art. The compounding can be accomplished with the aid of pill, tablet, presses, capsule mills and by other similar processes and equipment known to those skilled in the art. In addition, the composition may be formulated as a slurry or dispersion in aqueous media. This form will be a syrup, elixer or similar fluid delivery system containing a concentrated amount of the composition. It is preferred, however, to prepare the composition in dry form.

The composition of the invention is useful for restoration of proper inorganic ion electrolyte balance of the extracellular fluid in animals, mammals, and especially humans. It can act as a dietary supplement providing a substantial number of the minerals needed for efficient physiological function. The composition is in addition therapeutically useful for treatment of certain malconditions arising from electrolyte imbalance and from fluid retention. Specifically, the composition may be used to treat metabolic acidosis from renal disfunction, ketoacidosis and diarrhea. Concomitantly, the composition will restore the proper pH of extracellular fluid exhibiting acidosis, especially the blood. Symptoms associated with acidosis, such as diarrhea, nausea, gastrointestinal distress and the like are alleviated.

The composition may furthermore be used to treat tissue swelling associated with such diseases as portal hypertension, peritoneal inflammatory diseases, cirrhosis, hepatic congestion, peritoneal neoplastic disease and the like. Although the composition does not provide a curative treatment for these diseases, it does alleviate the fluid retention symptom associated with them. For example, it will ameliorate the symptoms of ascites associated with neoplastic disease or cirrhosis as well as ascites associated with other pathological conditions.

Anemia is another disease symptom which can be corrected by administration of the composition of the invention. Here again, although the composition is not a curative treatment for the underlying disease causing anemia, it will enrich the extracellular fluid with physiological iron so that production of hemoglobin may proceed efficiently.

To provide effective therapeutic treatment of the foregoing symptoms, it will be generally beneficial to administer oral doses of about 1-2 g per day of the composition. Dosage is best performed by administering periodic amounts of the composition throughout the day which are calculated to yield a total dose of about 1-2 g per day. Nevertheless, the regimen of treatment may be augmented or modified to conform with the patient's individual need and condition according to the judgment of his attending physician.

The composition of the invention has been demonstrated to have a low toxicity in mice and has little or no teratological efforts when administered to mice and rats over a short period. In the toxicity studies, the $LD_{50}$ of a 10 percent suspension of the composition in water was found to range from about 3100-3300 mg. per kg when administered by intraperitoneal injection to 60 day old mice. On the other hand, a 30 percent suspension of the composition did not show toxicity at doses as high as 8000 mg per kg when injected subcutaneously.

Teratological studies of the composition were accomplished by orally administering the composition to groups of pregnant mice and rats over a period of 6 days starting 7 days after copulation. The doses administered to the various groups were 1000, 3000 and 5000 mg per kg, in addition, control groups receiving no composition were also used.

The results of the teratological studies showed that the composition of the invention caused no significant adverse deviation from the normal physiological, morphological and biological patterns of the control groups. Specifically, the following comparisons between experimentals and controls were made:

1. net weight gains of dams were about the same;
2. no dam visceral abnormalities were observed;
3. resorption percentage of fetus was about the same;
4. weight gains of birthed young were higher for experimentals;

5. no fetal or newborn morphological or skeletal abnormalities were observed;
6. birth rate and viability of young were about the same. These studies also provided an indication of oral toxicity. The composition was shown to have no oral toxicity at doses as high as 5000 mg per kg.

The invention is further illustrated by the following examples.

EXAMPLE 1

Production of Wood Ash

Three-year old hickory trees in full bloom and completely leafed were extracted from the soil by use of a mechanical digger which removed the trees and roots to a depth of 4 feet. The trees were washed to remove excess dirt and then chipped in a circular hammer mill. The chips were fed to a grinder where they were converted to finely divided wood powder. The wood powder was collected and tumble dried by warm forced air means.

Ten kg of the powder was combusted to produce the ash ingredient of the composition. This portion was placed in a stainless steel retort vessel equipped with thermometer, an air inlet and outlet and a cooling means. A fritted tube led from the air inlet to below the powder surface. Air passage was started and combustion initiated by heating the surface of the powder with infrared radiation. Combustion was maintained by the passage of air and the temperature was controlled to less than 800° C. by a forced air bath surrounding the steel retort. Combustion was completed in about 30-180 minutes or when exit gases no longer tested positive for carbon dioxide (lime water test).

The ash (2.3 kg) was removed from the retort, combined with 18.4 kg of calcium carbonate and the mixture ground in a ball mill to produce a composition powder of 100-200 mesh. The composition powder was then fed into a tableting machine where portions were compressed to form 100 or 150 mg tablets. Excipients and diluents such as lactose, starch, gum acacia, sugar and the like may also be combined with the formulation according to the pharmacist's art.

A tableted composition produced in this manner had the following elemental analysis: total calcium—about 55.07% (as the oxide and carbonate), potassium oxide—about 10.39%, magnesium oxide—about 5.87%, phosphorus oxide—about 3.71%, sodium oxide—about 2.26%, manganese oxide—about 1.38%, aluminum oxide—about 0.87%, silicon dioxide—about 0.82%, ferric oxide—about 0.61% and germanium oxide—about 0.005%.

EXAMPLE 2

Use of Composition Tablets to Reduce Ascites

A patient suffering from ascites related to peritoneal neoplasm can be treated with the tablets made according to Example 1. The patient can be given about 4 doses a day each dose providing about 500 mg per kg of composition or 4-100 mg tablets per patient kg per dose. The size of the peritoneal swelling can be periodically measured by determining the torso circumference. In this manner the decrease in swelling can be determined. Tests of this kind can show that the composition of the invention is able to significantly reduce the amount of ascites swelling through a regular dosing regimen. The reduction may typically become readily noticeable after about 3-5 days administration of the composition.

EXAMPLE 3

Alleviation of Acidosis

A patient suffering from metabolic acidosis may be given periodic doses of the tablets prepared according to Example 1 in order to increase the pH of his blood. Doses of about 1.5 g per kg per day in 3 or 4 administrations will be appropriate.

The blood pH can be determined on a daily basis by removing a small quantity of venous blood from the patient and checking the pH in an autoanalyzer. This method will typically show that within about 3-5 days, the pH of the patient's blood may return to normal pH levels. It may be common, also, that the patient will no longer complain of nausea, diarrhea, and gastrointestinal distress associated with acidosis.

What is claimed is:

1. A pharmaceutical composition of essential minerals comprising wood ash particles of about 100 to 200 mesh size derived from whole hardwood trees in combination with calcium carbonate in a weight ratio of about 8:1 to about 9:1 respectively.

2. A pharmaceutical composition according to claim 1 in the form of an aqueous dispersion having a pH of from about 9 to 11.

3. A pharmaceutical composition according to claim 1 wherein the wood ash comprises a powdered residue produced by combusting ground, whole hardwood trees in an excess of oxygen or air and at a temperature of less than 800° C.

4. A composition according to claim 1 wherein the essential minerals contained in the composition comprise at least one member selected from inorganic compounds of calcium, magnesium, maganese, iron, aluminum, potassium, sodium, silicon, phosphorus, copper, zinc, cobalt, titanium, germanium and chromium.

5. A composition according to claim 4 wherein the inorganic compounds are present as oxides, halides or the oxidized forms of phosphorus and sulfur.

6. A composition according to claim 4 wherein the minerals present in the composition are oxides of calcium, potassium, magensium, phosphorus, sodium, manganese, aluminum, silicon, iron or germanium.

7. A pill, tablet or capsule containing a composition according to claim 1.

8. A composition according to claim 1 further comprising germanium oxide.

9. A method for treatment of peritoneal ascites in an animal comprising orally administering to said animal a composition according to claim 1 in an amount which is effective for treating peritoneal ascites.

10. A method according to claim 9 wherein the effective amount is about 1 to 2 g per kg per day.

* * * * *